United States Patent
Tavallaei et al.

(10) Patent No.: US 10,441,374 B2
(45) Date of Patent: Oct. 15, 2019

(54) SYSTEM FOR CATHETER MANIPULATION

(71) Applicants: Mohammad Ali Tavallaei, London (CA); Maria Drangova, London (CA)

(72) Inventors: Mohammad Ali Tavallaei, London (CA); Maria Drangova, London (CA); Michael Konstantine Lavdas, London (CA); Jeffrey Bax, London (CA); Aaron Fenster, London (CA)

(73) Assignees: Mohammad Ali Tavallaei, London (CA); Maria Drangova, London (CA)

( * ) Notice: Subject to any disclaimer, the term of this patent is extended or adjusted under 35 U.S.C. 154(b) by 384 days.

(21) Appl. No.: 15/517,629

(22) PCT Filed: Oct. 8, 2015

(86) PCT No.: PCT/US2015/054665
§ 371 (c)(1),
(2) Date: Apr. 7, 2017

(87) PCT Pub. No.: WO2016/057778
PCT Pub. Date: Apr. 14, 2016

(65) Prior Publication Data
US 2017/0304015 A1    Oct. 26, 2017

Related U.S. Application Data (60) Provisional application No. 62/061,264, filed on Oct. 8, 2014.

(51) Int. Cl.
*A61B 34/30* (2016.01)
*A61M 25/01* (2006.01)
(Continued)

(52) U.S. Cl.
CPC .............. *A61B 34/35* (2016.02); *A61B 34/20* (2016.02); *A61B 34/30* (2016.02); *A61B 34/37* (2016.02);
(Continued)

(58) Field of Classification Search
CPC ......... A61B 34/35; A61B 34/20; A61B 34/37; A61B 2034/301; A61B 34/76; A61B 34/2034; A61B 34/2051; A61M 25/0133
See application file for complete search history.

(56) References Cited

U.S. PATENT DOCUMENTS

| | | | |
|---|---|---|---|
| 6,058,323 A | 5/2000 | Lemelson | |
| 6,375,471 B1 | 4/2002 | Wendlandt et al. | |

(Continued)

FOREIGN PATENT DOCUMENTS

EP    1950346 A2    4/2008

OTHER PUBLICATIONS

International Search Report for corresponding International Application No. PCT/US2015/054665 dated Jan. 25, 2016; 5 pages.
(Continued)

*Primary Examiner* — Jason E Flick
*Assistant Examiner* — Courtney B Fredrickson
(74) *Attorney, Agent, or Firm* — Patterson Thuente Pedersen, P.A.

(57) ABSTRACT

Embodiments relate to systems and methods for catheter manipulation. In particular, systems as described herein can be used to drive a catheter while maintaining control along three degrees of freedom. Systems as described herein can be used in a wide variety of settings, including MRI in which small, non-magnetic robot systems having motors that remain stationary during use are advantageous.

11 Claims, 9 Drawing Sheets

(51) Int. Cl.
*A61B 34/35* (2016.01)
*A61B 34/00* (2016.01)
*A61B 34/20* (2016.01)
*A61B 34/37* (2016.01)
*A61B 90/00* (2016.01)

(52) U.S. Cl.
CPC ......... *A61B 34/76* (2016.02); *A61M 25/0113* (2013.01); *A61M 25/0136* (2013.01); *A61B 2034/2051* (2016.02); *A61B 2034/301* (2016.02); *A61B 2090/065* (2016.02); *A61M 2205/0216* (2013.01)

(56) References Cited

U.S. PATENT DOCUMENTS

| | | | |
|---|---|---|---|
| 7,789,874 | B2 | 9/2010 | Yu et al. |
| 9,387,289 | B2* | 7/2016 | Swan .................. A61M 5/1454 |
| 2004/0254566 | A1* | 12/2004 | Plicchi .................. A61B 34/70 606/1 |
| 2006/0173239 | A1 | 8/2006 | Neumann et al. |
| 2009/0082722 | A1 | 3/2009 | Munger et al. |
| 2010/0305502 | A1 | 12/2010 | Ferry et al. |
| 2011/0040150 | A1* | 2/2011 | Govari .................. A61B 34/30 600/117 |
| 2011/0060346 | A1 | 3/2011 | Jensen et al. |
| 2012/0184955 | A1 | 7/2012 | Pivotto et al. |

OTHER PUBLICATIONS

Written Opinion of the International Searching Authority for corresponding International Application No. PCT/US2015/054665 dated Jan. 25, 2016; 8 pages.

International Preliminary Report on Patentability for corresponding International Application No. PCT/US2015/054665 dated Apr. 11, 2017; 9 pages.

Tavallaei et al., "Design, development and evaluation of a compact telerobotic catheter navigation system," The International Journal of Medical Robotics and Computer Assisted Surgery (Nov. 3, 2015) 12; 442-452.

Tavallaei et al, "Magnetic resonance imaging compatible remote catheter navigation system with 3 degrees of freedom," Int J CARS (Dec. 24, 2015) 11 (8); 1-9.

* cited by examiner

SYSTEM FOR CATHETER MANIPULATION

CROSS-REFERENCE TO RELATED APPLICATIONS

The present application is a National Phase entry of PCT Application No. PCT/US2015/054665, filed on Oct. 8, 2015, which claims the benefit of U.S. Provisional Application No. 62/061,264 filed Oct. 8, 2014, which are hereby fully incorporated herein in their entireties by reference.

TECHNICAL FIELD

Embodiments relate generally to devices for introducing media such as a catheter into the body. More particularly, embodiments relate to a robotic system used to manipulate a catheter. A tele-robotic system allows the remote manipulation of a conventional steerable catheter with three degrees of freedom, in embodiments.

BACKGROUND

Catheterization is a procedure in which a catheter is inserted in to the vasculature and navigated to a desired target location in the cardiovascular system for the purposes of delivering therapy or diagnosis. For example in the treatment of atrial fibrillation, as a typical application, an ablation catheter would be introduced to the vasculature and navigated to the left atrium to deliver RF ablation to desired anatomical locations in order to electrically isolate the source of arrhythmia from the rest of the heart.

Catheterization is conventionally guided by fluoroscopy. Fluoroscopy provides two-dimensional projections of the anatomical site, but low soft tissue contrast and the potential for spread of harmful radiation are undesirable aspects of conventional fluoroscopy-guided catheterization. Radiation spread is particularly a hazard for interventionalists who perform this procedure for prolonged periods of time on a daily basis. In contrast to fluoroscopy, Magnetic Resonance Imaging (MRI) is a safe imaging modality that offers superior soft-tissue-contrast, allows for 3D visualization and allows for monitoring of temperature elevations as well as the potential of identifying infarct and ischemic tissue. A challenge to MRI guided catheterization, however, is that the bore of conventional closed-bore MRI scanners is smaller and greatly limits patient access, which can hinder many procedures.

Conventional catheterization systems are commercially available, in which a catheter is driven by a robot or other remote device. Most conventional remote catheterization systems have the ability to manipulate a catheter with 2 degrees of freedom. Some remote catheterization systems have the ability to manipulate a catheter with 3 degrees of freedom. Neither of these systems, however, is appropriate for use in MRI settings, due to the magnetic materials of which they are made.

Some conventional catheterization systems are unable to accept catheters of various standard sizes, and must be used with catheters specific to the particular system. Among those that do accept standard-sized catheters, often only one standard size can be manipulated by the robot.

Furthermore, in many conventional systems, the motor itself moves with the catheter. This can restrict range of motion and also be detrimental in systems for use in, for example, MRI settings, in which operating space is relatively small and magnetic and current-carrying components should be kept out of some regions.

A system that allows for remote manipulation of a conventional patient catheter is therefore needed. Such a system should be fully non-magnetic, and should be configured for use in remotely navigating a conventional off-the-shelf catheter under the guidance of conventional fluoroscopy images and electromagnetic tracking systems, or inside the bore of an MRI scanner during MR imaging.

SUMMARY

Embodiments of the present application substantially address or meet the aforementioned needs of the industry. In an embodiment, a system and method are provided for remotely manipulating a conventional steerable catheter. The system allows for simultaneous manipulation of the catheter body and the catheter handle to allow for the navigation of the catheter tip with three degrees of freedom.

In embodiments, a differential gear mechanism is incorporated, such that compact catheter manipulation can be achieved both axially and radially. The differential gear mechanism of this embodiment allows keeping the position of the motors fixed during catheter manipulation.

In embodiments, a winch and a lever mechanism are incorporated such that a plunger of the catheter can be manipulated, and the catheter can be steered while the catheter handle is rotated.

In embodiments, a master system includes a user interface such that the catheter handle can be moved axially and rotated. The plunger of the catheter can also be manipulated. All the motions applied on the catheter can be measured by sensors such as optical encoders, in embodiments, and provided as references to a control system.

In embodiments, the actuators of a system are non-magnetic ultrasonic motors and a robot is fully made of non-magnetic material. Therefore, the system can be used inside the bore of an MRI system, and the user can remotely navigate a catheter or other components of the system using MRI data for positioning guidance.

In embodiments, the actuators can be a conventional DC or stepping motor, and the robot can be used to perform remote catheter navigation under conventional fluoroscopy and electromagnetic tracking guidance.

BRIEF DESCRIPTION OF THE DRAWINGS

Embodiments may be more completely understood in consideration of the following detailed description of various embodiments in connection with the accompanying drawings, in which:

FIGS. 4-6B are perspective views of a compact catheter manipulator according to embodiments.

FIGS. 7A-7F depict a differential gear mechanism in a compact catheter manipulator according to an embodiment.

While embodiments are amenable to various modifications and alternative forms, specifics thereof have been shown by way of example in the drawings and will be described in detail. It should be understood, however, that the intention is not to be limited to the particular embodiments described. On the contrary, the intention is to cover all modifications, equivalents, and alternatives falling within the spirit and scope of the appended claims.

DETAILED DESCRIPTION

Tele-robotic systems as described herein facilitate full manipulation of a conventional off-the-shelf patient catheter with three degrees of freedom. Particular embodiments of such systems are described herein without limitation with respect to other embodiments.

Figure 1:
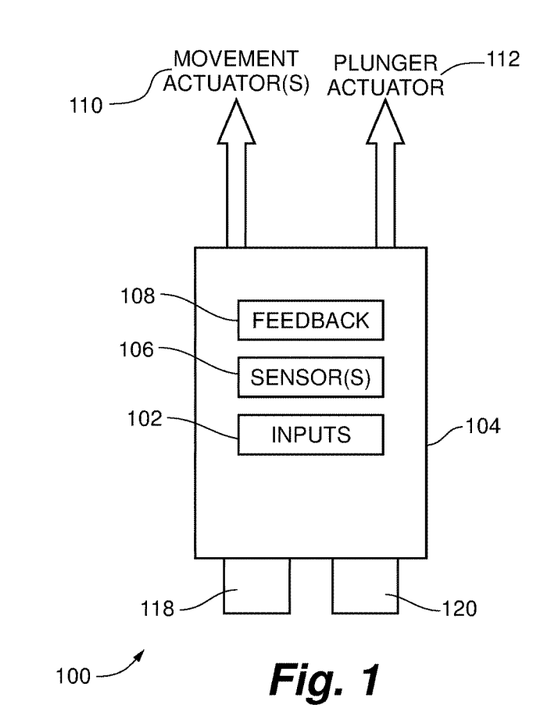
FIG. 1 is a schematic diagram of a master system for driving a catheter according to an embodiment.

FIG. 1 is a schematic diagram of a master system 100. Master system 100 includes inputs 102 and a housing 104, and is configured to send signals to various other components to act on a catheter, as described herein.

Master system 100 is a unit that facilitates measurement of an input and translates such input into axial motion, radial motion, and tip steering corresponding to a catheter. Master system 100 is further capable of detecting and/or transmitting the measured force from the catheter tip to the user by use of motors.

Master system 100 includes inputs 102, which can be, for example, a catheter handle, buttons, or some other input mechanism. In embodiments, inputs 102 can respond to analog input such as an amount of force applied to the handle. In embodiments, inputs 102 are mechanically coupled to housing 104, to allow for relative movement and/or rotation there between. Master system 100 further includes first motor 118 and second motor 120, coupled to housing 104.

Housing 104 provides a mechanical base upon which various other components of master system 100 are mounted. In the embodiment shown in FIG. 1, such other components include sensor(s) 106 and feedback provider 108, mounted in or on housing 104. As indicated by arrows, data entered at inputs 102 can be translated into signal sent to a movement actuator 110 and a plunger actuator 112, in embodiments.

Sensors 106 can be used to sense movement of housing 104, in embodiments. For example, in embodiments where housing 104 is movable based on inputs 102, sensor(s) 106 can detect such movement to verify that the quantity of movement is commensurate to that indicated at inputs 102. Sensor(s) 106 can be an optical encoder or encoders, in embodiments.

In the embodiment shown in FIG. 1, first motor 118 is configured not only to drive movement actuator(s) 110, but also in embodiments to provide haptic feedback for the user. For example, where movement actuator(s) 110 face resistance in advancing or rotating a catheter, such resistance can be sensed by first motor 118 and indicated at inputs 102 (for example by making movement of a handle or other input 102 more difficult).

Second motor 120 can also be operatively coupled to inputs 102, and second motor 120 can also be controlled to provide haptic feedback at inputs 102 based on force information feedback from a remote catheter tip (not shown). In embodiments, second motor 120 is mechanically coupled to inputs 102 and plunger actuator 112, or a plunger actuator assembly such as those described herein with respect to FIG. 3.

First motor 118 and second motor 120 can each be controlled by sensor(s) 106, in embodiments. In particular, there may be a predetermined maximum range in which first motor 118 and second motor 120 should operate to perform a procedure. In other embodiments, sensor(s) 106 can measure when a maximum range of motion corresponding to the catheter or other components is about to be reached, and stop motion accordingly. In embodiments, a stop of motion caused by sensor(s) 106 can be broadcast to a user of system 100, either haptically or through some other means such as an alarm sound or a light.

First motor 118 and second motor 120 can use piezoelectric actuators, or can be ultrasonic motors. As such, first motor 118 and second motor 120 can be made of non-magnetic materials, which are suitable for use in areas having relatively high magnetic fields, such as in an MRI. As such, the robot mechanical assembly can be made of sufficiently non-magnetic material that the entire robot (including the motors 118 and 120) can be placed within an MRI chamber.

In embodiments, a medical care professional can interface with a tele-robotic system for commanding the movement of a catheter via master system 100. In an embodiment, master system 100 can be used to measure the user's desired input reference motion imparted on an input catheter. These motions can include axial catheter motion, radial catheter motion and plunger manipulation.

Figure 2:
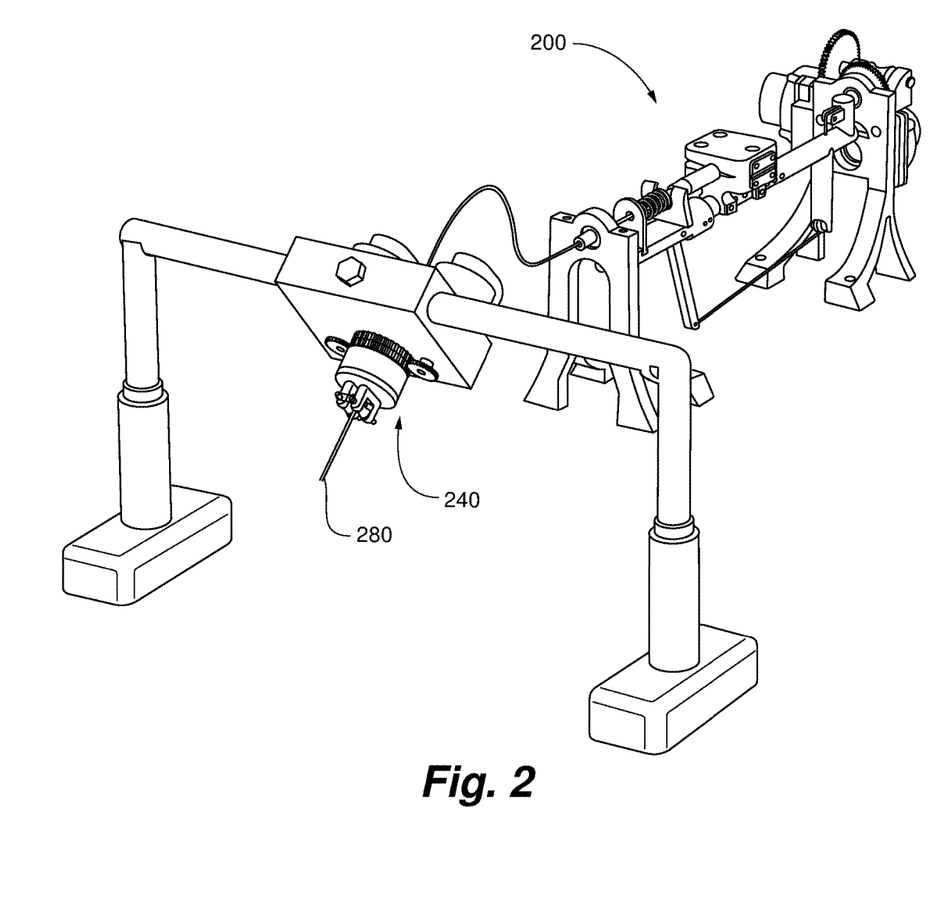
FIGS. 2 and 3 are perspective views of a two-part slave system for driving a catheter and activating a catheter plunger according to an embodiment.

FIG. 2 is a perspective view of a plunger actuator 200 and a compact catheter manipulator (CCM) 240, each coupled to a common catheter 280. CCM 240 is a slave or follower system, which can replicate or proportionally follow the motion imparted on a remote master system (e.g., master system 100 as previously depicted with respect to FIG. 1). In embodiments, plunger actuator 200 and/or CCM 240 can be made of one or more fully non-magnetic materials, such that they are suitable for use in an MRI setting. In an embodiment, plunger actuator 200 is configured to hold catheter 280, for example at a catheter handle (not shown), while CCM 240 manipulates catheter 280. These two components work together to manipulate catheter 280. Catheter 280 is a steerable catheter, such as an ablation catheter, and can be steered by actuating a plunger axially along the catheter handle. Plunger actuator 200 is shown in more detail in FIG. 3, while CCM 240 is shown in more detail in FIG. 4.

Figure 3:
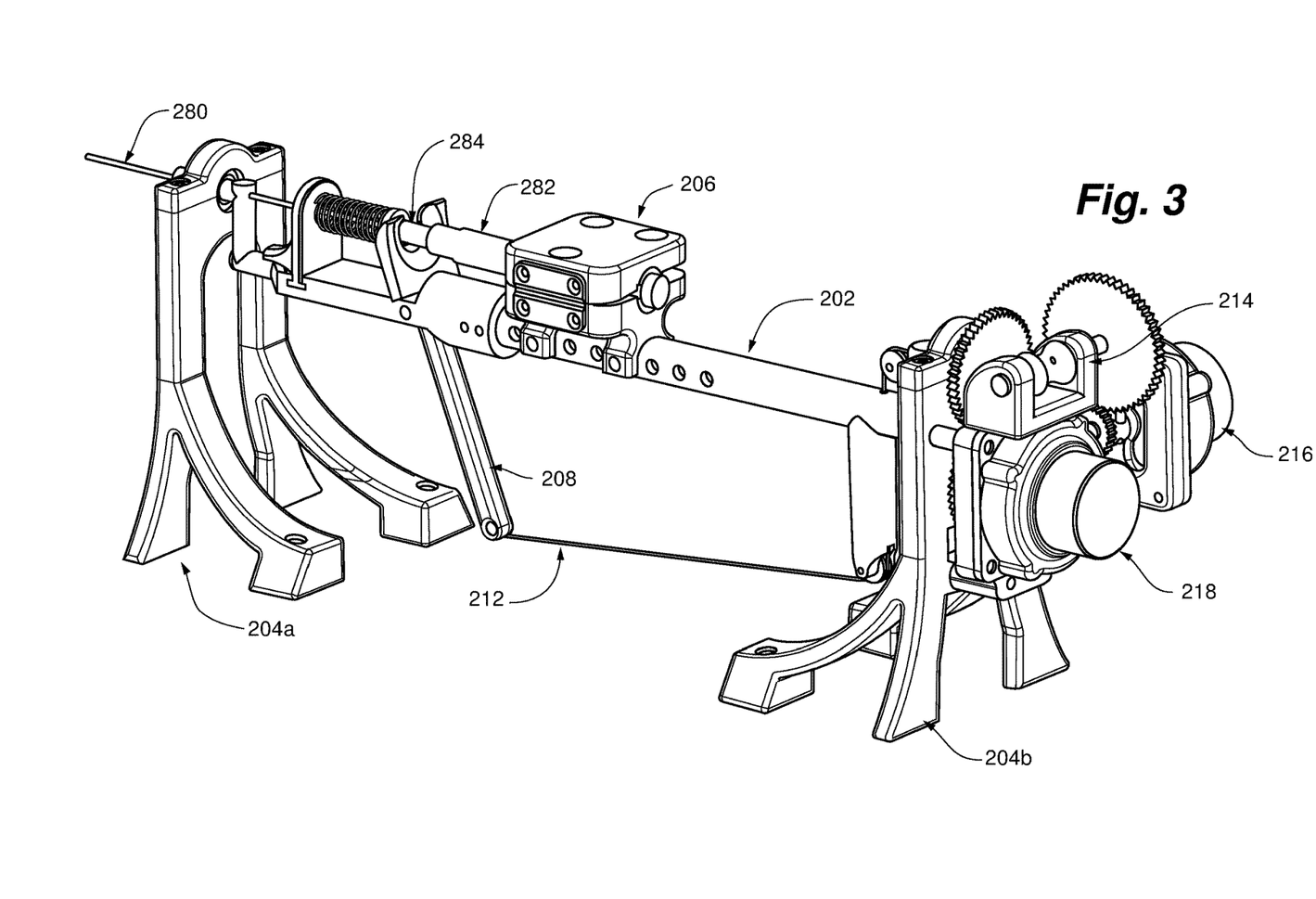

Referring now to FIG. 3, plunger actuator 200 includes a rotatable gantry 202 positioned between two support piers 204*a* and 204*b*. A catheter housing 206 is mounted on rotatable gantry 202. A fork 208, a spring 210, a line 212, and a winch mechanism 214 are mechanically coupled thereto. A first motor 216 to and a second motor 218 are mechanically connected to the aforementioned components to drive a catheter 280. Catheter 280 includes a catheter handle 282 and a catheter plunger 284. Plunger actuator 200 can hold patient catheter handle 282 and actuate catheter plunger 284 to allow for steering a distal end of a steerable catheter 280 (not shown). Embodiments as described herein can act on catheters having built-in catheter plungers. In alternative embodiments, plunger actuator 200 can provide other actuation mechanisms for routing a fluid through catheter 280, or some other catheter that does not have a built-in catheter plunger. For example, in alternative embodiments, plunger actuator 200 could be configured to actuate a plunger in a hub that receives a catheter without a built-in plunger.

Plunger actuator 200 includes rotatable gantry 202 mounted on two supporting piers 204*a* and 204*b*. In the embodiment shown in FIG. 3, catheter handle 282 is mechanically coupled to rotatable gantry 202, and is secured at catheter housing 206. Furthermore, in the embodiment depicted in FIG. 3, catheter plunger 284 is positioned between fork 208 and spring 210. Line 212 can be actuated via winch 214, which is operable by first motor 216. In operation, as winch 214 winds up line 212, fork 208 is pulled and catheter plunger 284 is pushed forward, causing spring 210 to retract. When the winch 214 winds out, spring 210 pushes catheter plunger 284 back, relaxing the distal end of the catheter 280.

Housing 206 is coupled to rotatable gantry 202 and holds catheter handle 282 relative thereto. Rotatable gantry 202 is coupled to second motor 218 such that the rotation of second motor 218 results in the rotation of gantry 202 and therefore catheter handle 282. Housing 206, gantry 202, and various other components are supported by support piers 204a and 204b. In the embodiment depicted in FIG. 3, support piers 204a and 204b comprise a non-magnetic substance. For example, support piers 204a and 204b can be made of a polymeric material. Despite the relatively flexible, breakable, and/or brittle natures of many non-magnetic materials, the arched design of support piers 204a and 204b shown in FIG. 3 can provide sufficient structural support for the various components of plunger actuator 200, including the motors and other systems, as well as provide support for plunger actuator to apply external forces (e.g., when acting upon catheter 280).

Plunger actuator 200 depicted in FIG. 3 is capable of acting on catheter 200 to provide both rotational movement (via rotatable gantry 202) as well as plunger actuation (via fork 208, line 212, and winch 214). These functions can be controlled precisely, in embodiments, by using a motor or actuator having a desired level of precision and accuracy, such as first motor 216 and second motor 218.

Figure 4:
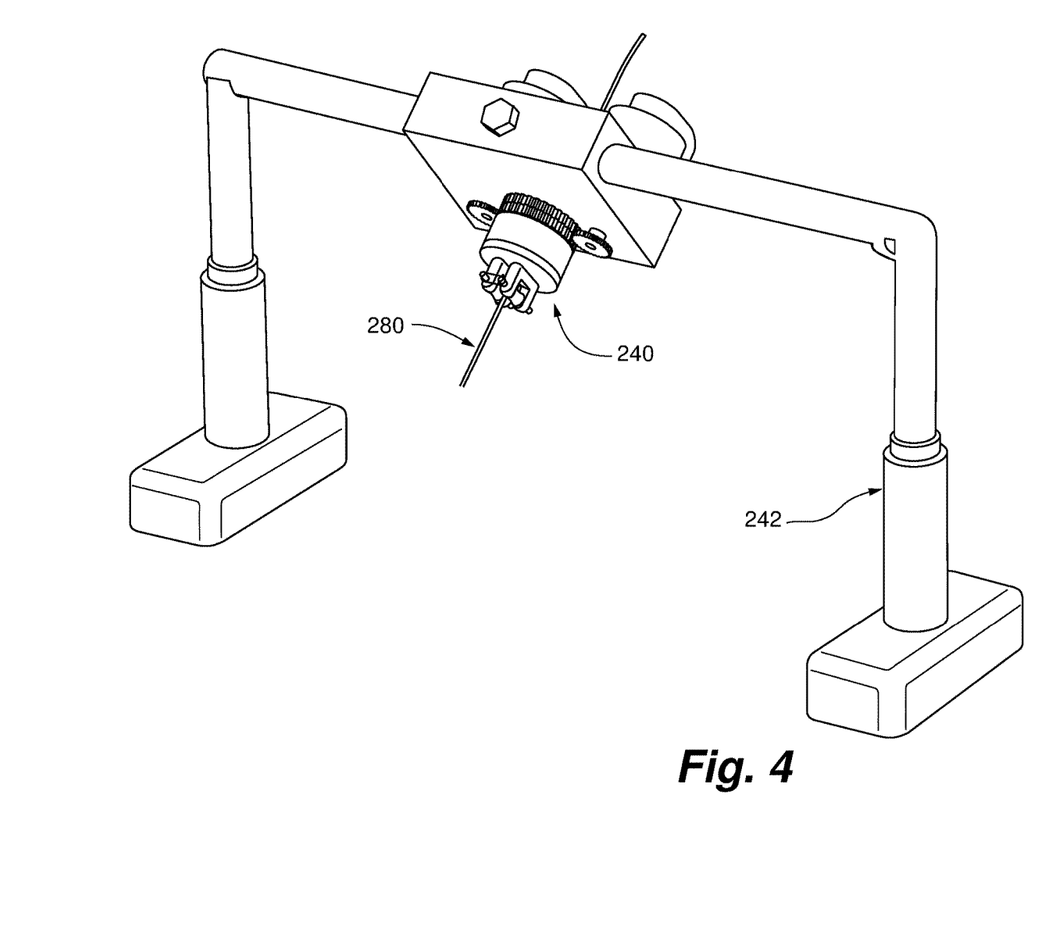

CCM 240 is configured to manipulate catheter 280 in still other modes, in the embodiment depicted in FIG. 4. Catheter 280 can be arranged through CCM 240, as shown in FIG. 4, and when positioned as such can be manipulated radially and/or axially by CCM 240. An adjustable mount 242 allows for desired positioning of CCM 240 at or near the catheter point of entry into, for example, the patient body. CCM 240 is shown on adjustable mount 242 in FIG. 4.

Figure 5:
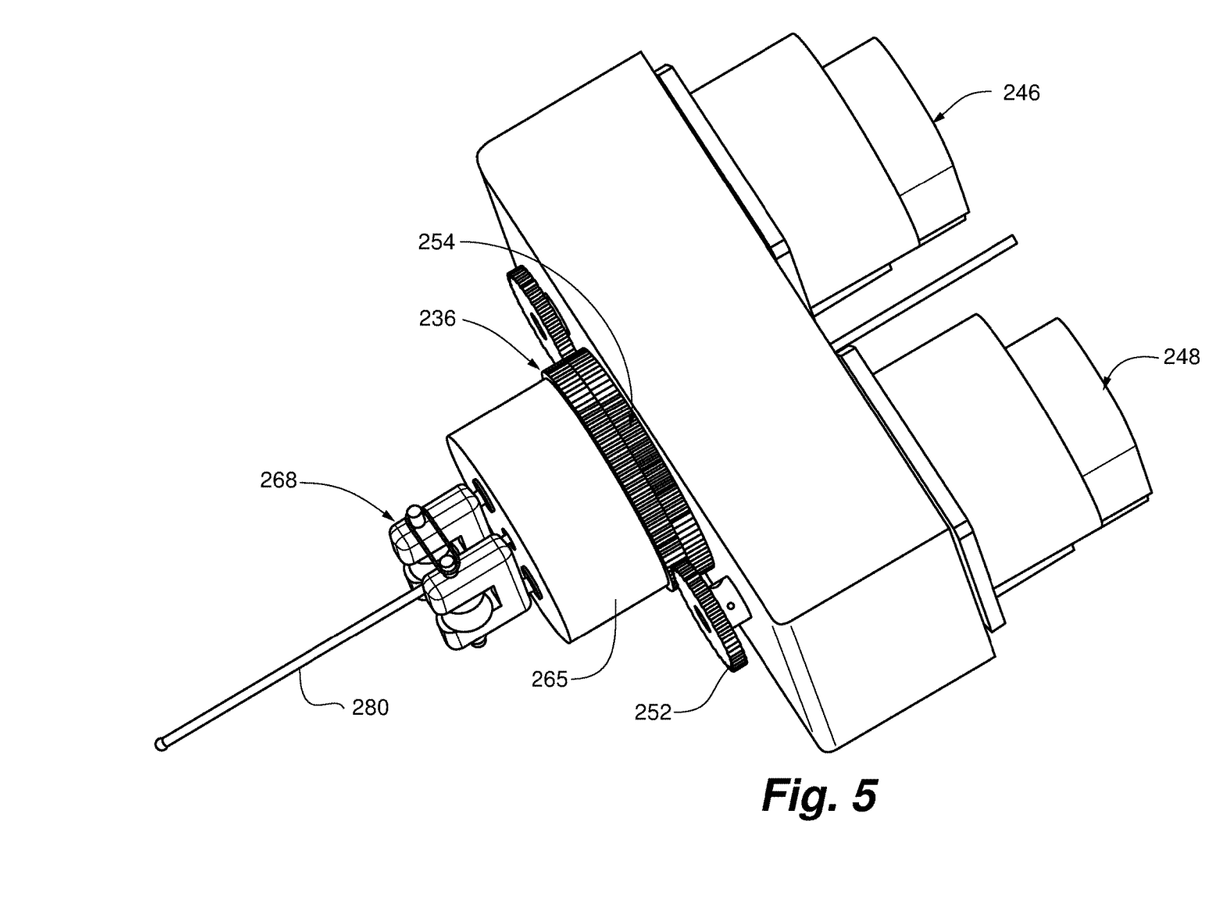
Figure 6A:
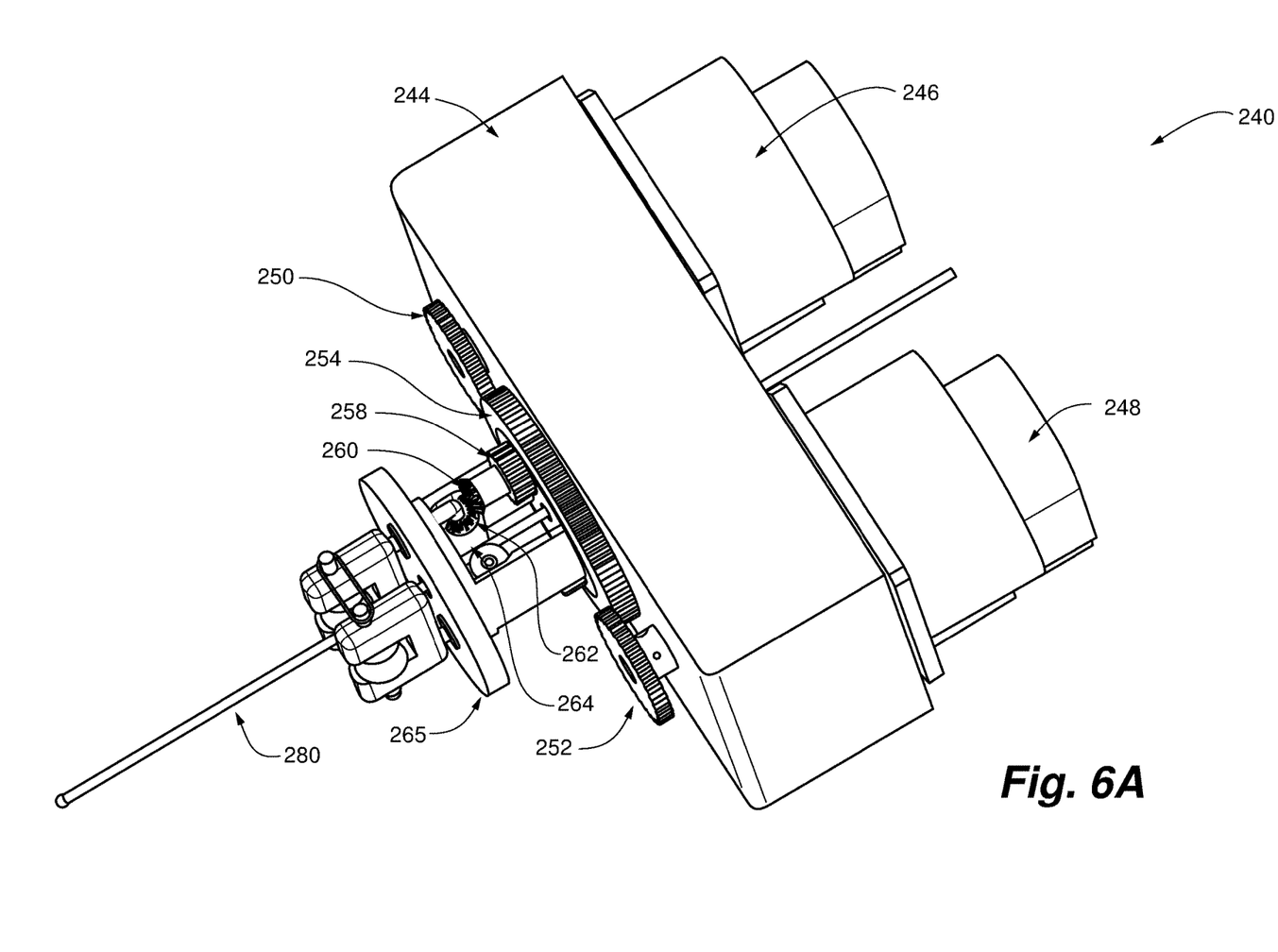
Figure 6B:
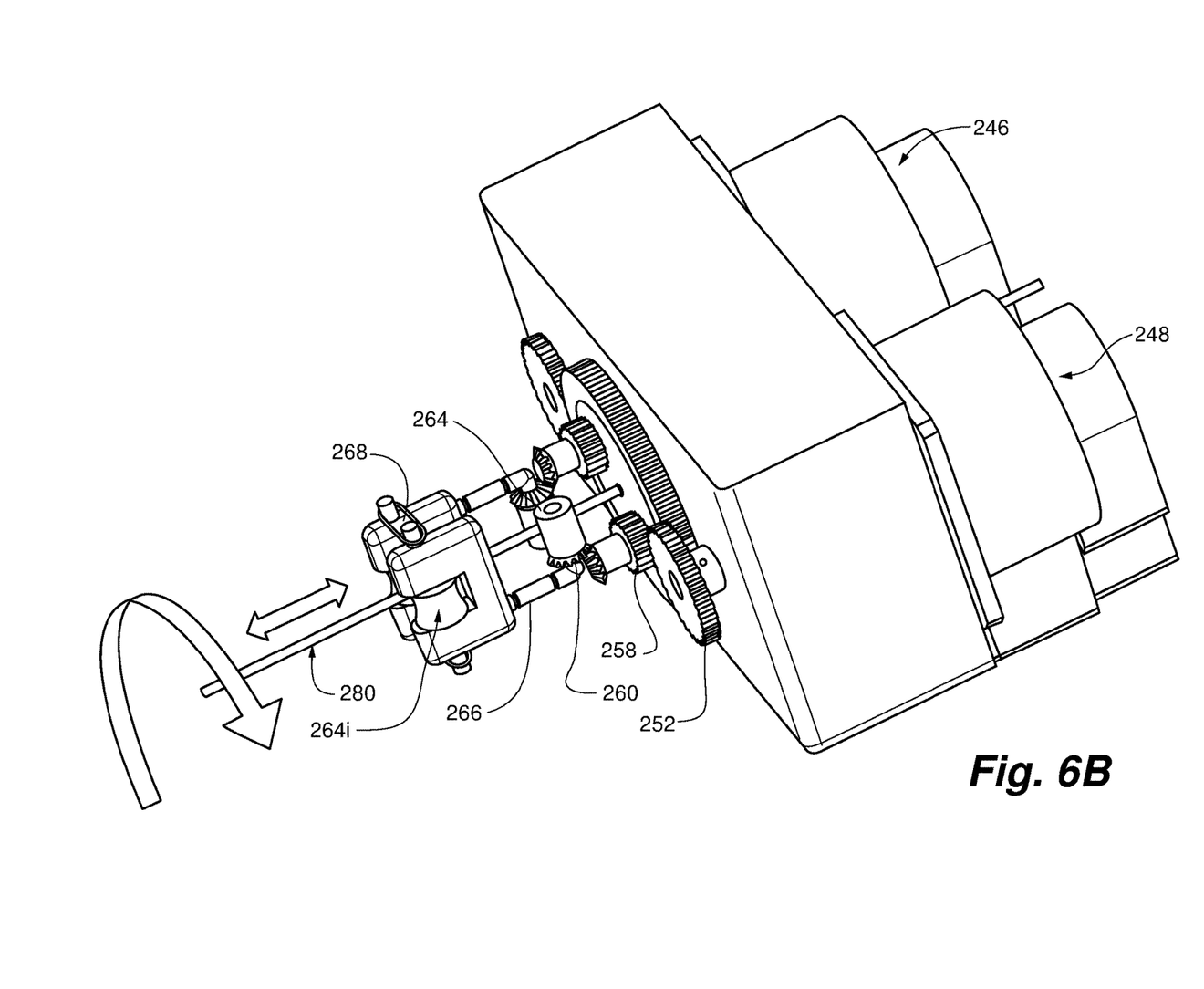

CCM 240 makes use of a differential gear mechanism to allow for axial and radial manipulation of catheter 280 with the source of actuation (motor positions) fixed, in embodiments, as depicted in FIGS. 5 and 6. CCM 240 can be used with catheters 280 of various sizes. For example, in one embodiment CCM 240 can be used with any catheter having a size between about 3 Fr and about 15 Fr, though smaller and larger catheters can be used in other embodiments. In embodiments, CCM 240 can be used with any catheter having a size between about 5 Fr and about 10 Fr. In embodiments, CCM 240 can be adjustable to be used with any catheter having a size between 0 Fr and 20 Fr. As described in more detail below, CCM 240 is able to accommodate a wider variety of sizes of catheters than conventionally available systems.

As shown in FIGS. 5 and 6A, CCM 240 includes a base 244, a third motor 246, and a fourth motor 248. CCM 240 further includes drive gears 250 and 252, which are attached to the third motor 246 and fourth motor 248. Drive gears 250 and 252 are coupled to a base gear 254 and a ring gear 256, respectively. Ring gear 256 drives planet gears 258, miter gears 260 and 262, and rollers 264. FIG. 5 additionally depicts housing 265, which is partially removed along with ring gear 256 in the view shown in FIG. 6A to more clearly illustrate the internal gears and rollers of CCM 240.

Base 244 is coupled to third motor 246 and fourth motor 248. In embodiments, base 244 includes axles or other structures for transmission of the output of third and fourth motors 246, 248 to drive gears 250, 252, respectively. Drive gear 250 can engage with third motor 246 to provide rotation of CCM 240. Drive gear 252 can engage with fourth motor 248 to provide further manipulation of catheter 280. By manipulating drive gear 250, base gear 254 can be rotated. Because base gear 254 forms a platform on which the other geared systems described and shown herein are arranged, rotation of base gear 254 causes rotation of all the components of CCM 240 that are arranged opposite base 244 from base gear 254. This includes all of the geared systems as well as the rollers 264 that hold catheter 280. As such, rotation of base gear 254 causes rotation of catheter 280.

Manipulation of drive gear 252 causes rotation of ring gear 256. Within ring gear 256 are planetary gears 258 that are positioned with their rotation axis perpendicular to the outer surface of base gear 254, to which they are mounted. Each of the planetary gears 258 is further coupled to at least one miter gear 260 arranged concentrically and rigidly attached to the planetary gear 258. The miter gears 260 are arranged to engage with other miter gears 262 positioned parallel to the other surface of base 244. The miter gears 262 are arranged parallel with the outer surface of base 244 and are in contact with catheter 280 via rollers 264. Rollers 264 can be, for example, rubber rollers in one embodiments. The rotation of miter gears 262 with respect to their own axis is proportional to the difference of rotation between base gear 254 and ring gear 256, as shown in the depicted embodiment. The double-sided ring gear 236 engages with the fourth motor 248 and with miter gears 258 perpendicular to the base 254 on the inside. FIG. 6B shows CCM 240 with the remainder of housing 265 removed. In this view, the relationship between the geartrains can be more easily seen. Furthermore, as shown in FIG. 6B, in embodiments there can be active rollers 264 as well as idle rollers 264i. This combination of rollers can provide further support to catheter 280 as it is moved either rotationally or axially, as indicated by the arrows.

Referring now to FIGS. 7A-7F, CCM 240 is shown in more detail. In particular, those features of CCM 240 that facilitate use of catheter 280 having a diameter within a broad range are shown. As shown in FIGS. 7A-7F, CCM 240 includes a series of geared connections between motors 246, 248 and catheter 280. In particular, third motor 246 can power a geartrain from drive gear 250 to base gear 254, which affects rotational position of catheter 280. Likewise, fourth motor 248 can power a geartrain from drive gear 252 to ring gear 256, to planetary gears 258, to miter gears 260, to rollers 264 to affect longitudinal movement of catheter 280.

Figures 7A, 7B, 7C, 7D, 7E, 7F:
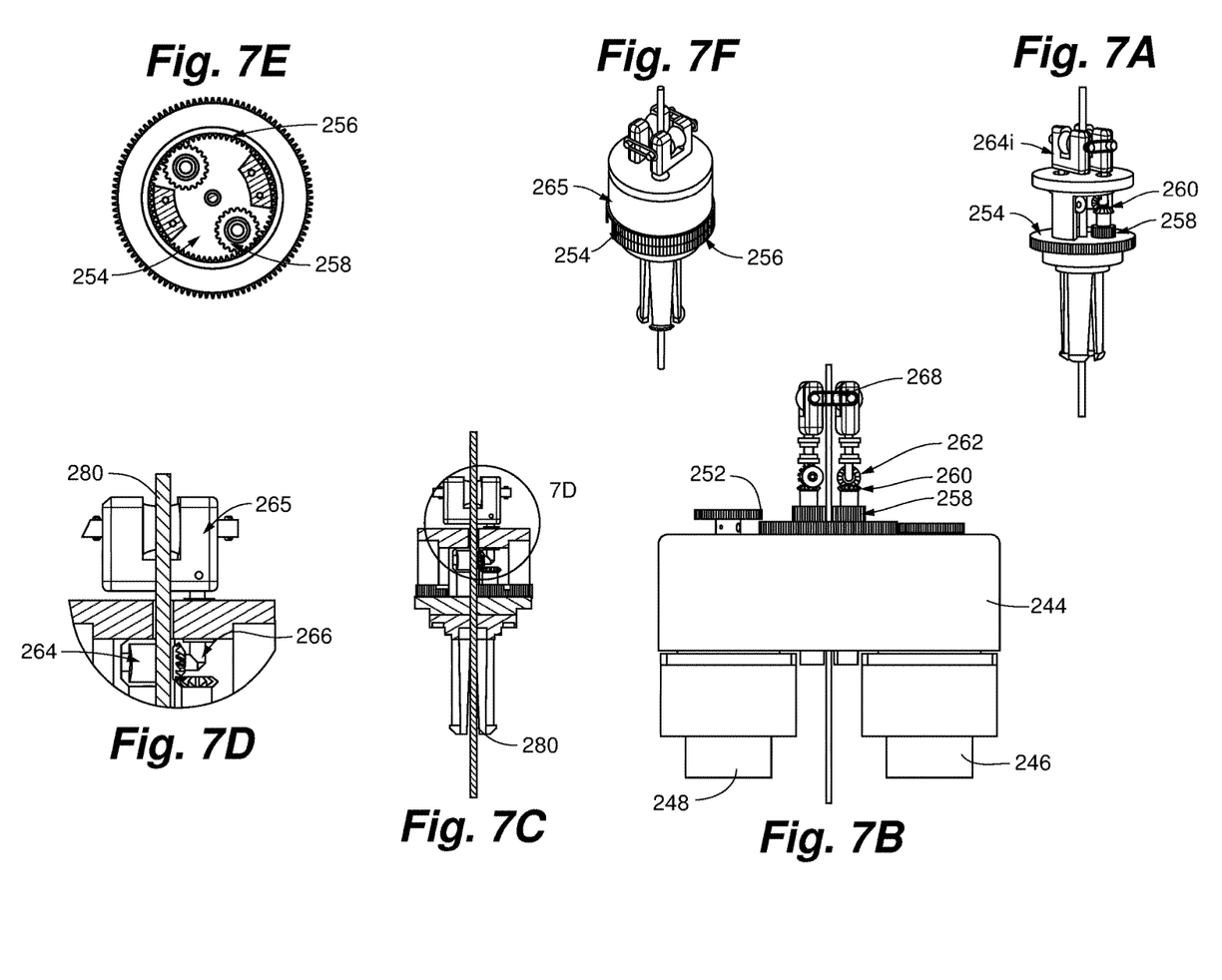

As shown in FIGS. 7A-7F, miter gears 260 can rotate along the axis of corresponding miter gears 266. Each of miter gears 260 has a corresponding miter gear 266. The shaft of corresponding miter gears 260 extends, as shown in FIGS. 7C and 7D, outside the housing 265 and provides a means to hold to the shafts together. In the embodiment shown in FIGS. 7A-7F, the corresponding miter gears 266 are pulled towards one another by an elastomeric band 268, such that catheter 280 is sandwiched between the rollers 264. Elastomeric band 268 can expand or contract, and will apply a substantially constant force at any given level of stretch. As such, for a larger-sized catheter 280, elastomeric band 268 can be stretched such that rollers 264 are properly spaced, and elastomeric band 268 will provide compressive force on catheter 280 via rollers 268. Conversely, for a smaller-sized catheter 280, elastomeric band 268 can relax to accommodate the smaller catheter 280 while still providing sufficient compressive force on catheter 280 via rollers 268. In alternative embodiments, elastomeric band 268 could be replaced by any other device that applies force between the corresponding miter gears 266, such as a spring, clamp, or other similar object. In embodiments, this can be a "passive" device that applies a force according to Hooke's Law or an elastomeric device, whereas in alternative embodiments this could be a device such as a hand clamp that is manually tightened according to the desired level of force and distance between corresponding miter gears 266. In embodiments, corresponding miter gears 266 can be held together by any of a variety of such binding devices, or a combination thereof.

Elastomeric band 268 provides constant pressure on catheter 280 and, by providing access to corresponding miter gears 266 on the exterior of housing 265, changing and monitoring the status of elastomeric band 268 can be accomplished. For example, in embodiments where a smaller catheter 280 is to be used, a relatively "tighter" elastomeric band can be used, such as one having a higher spring constant or a smaller size. Constant pressure from elastomeric band 268 provides frictional contact between rollers 264 and the catheter/needle and hence reduces slippage and improves positioning accuracy.

Figure 8:
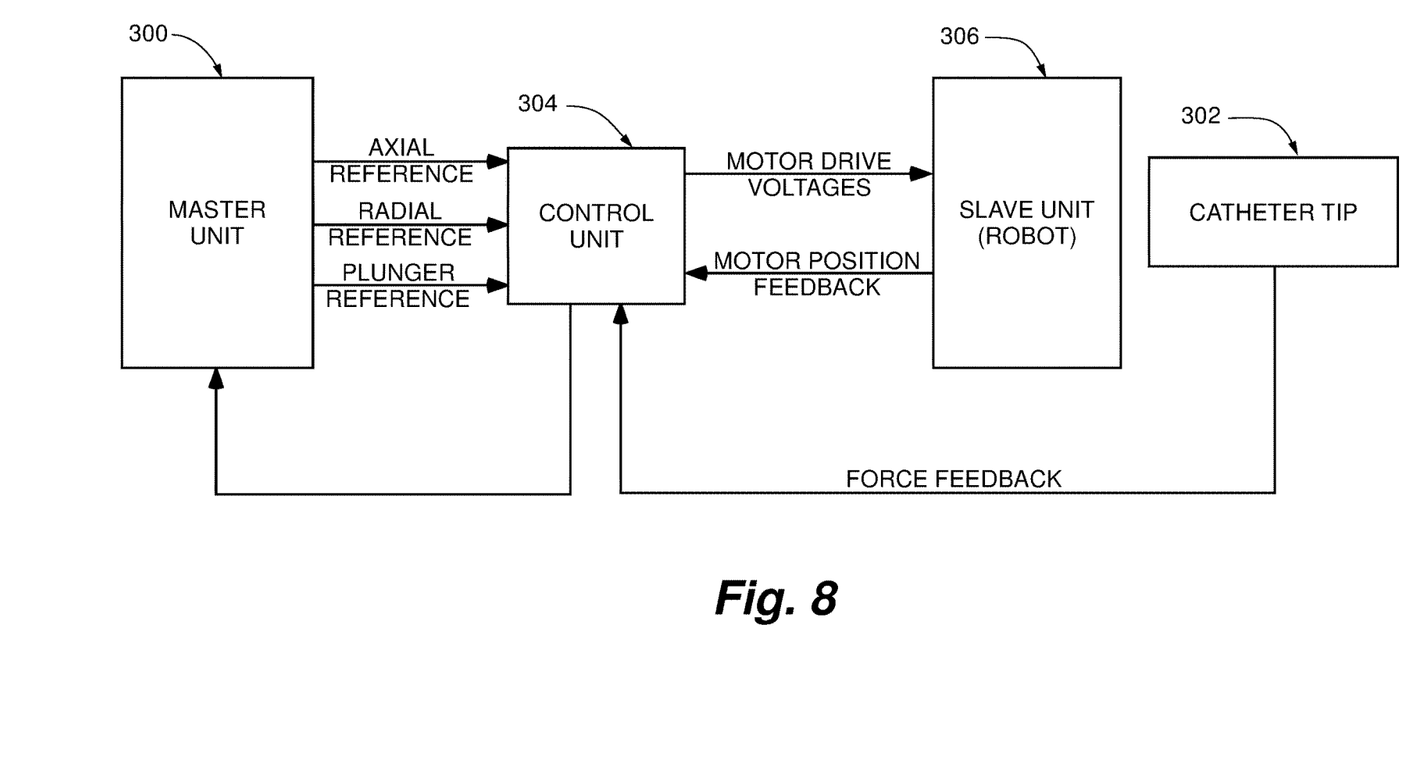
FIG. 8 is a schematic diagram depicting a method for operating a system for driving a catheter according to an embodiment.

Referring now to FIG. 8, a user such as a medical professional can manipulate the master unit 300 which captures a desired reference motion to be transferred to catheter 302. Such desired reference motion can include axial, radial, and plunger motion as indicated along the arrows. Such reference motion is transferred from the master unit to the control unit 304, for example by means of serial communication. Control unit 304 can use the reference motion to control robot 306 such that catheter 302 follows the user's desired reference motion imparted on the master unit 300. In an embodiment the reference motion can by multiplied by a constant and then used by the control unit 304 to control the robot 306 to control the motion of catheter 302. The constant can be a user-selectable scalar value, in embodiments. Such a scalar allows for amplification or reduction of the motion. For example, if the user manipulates the master unit 50 mm, a gain (scalar) of 0.1 will result in catheter motion of 5 mm. This will allow finer control in the catheter motion that may be useful for some applications. Alternatively, the gain can be larger than 1, which will result in motion amplification, which may be desirably in scenarios where faster motion is required. In an embodiment, the master unit 300 captures the force sensed at the tip of catheter 302, for example from a force sensor at the tip of catheter 302, and uses that sensed data to generate haptic feedback for the user through the master unit 300. In an embodiment control unit 304 senses force at the tip of catheter 302, for example from a force sensor at the tip of the catheter, to allow for automatic regulation of the catheter contact force by controlling the axial position of catheter 302.

More generally, a compact catheter manipulator can include a housing and a base gear configured to engage to define a cavity. The housing can include a ring gear portion, and a plurality of active rollers arranged within the cavity. The plurality of active rollers can be mounted to the base gear such that rotation of the base gear causes a corresponding rotation of the plurality of active rollers. The plurality of active rollers can be mechanically coupled to the ring gear such that rotation of the ring gear results in actuation of the active rollers. A plurality of idle rollers can be arranged outside the cavity, wherein the plurality of idle rollers are mounted to the housing such that rotation of the base gear causes a corresponding rotation of the plurality of idle rollers. The housing can be configured to be detachable from the base gear.

In such embodiments, the housing can provide a clean environment in which the various gears and rollers can function during an operation. After the operation is complete, or at any desired time, the housing can be removed and cleaned, or removed to provide access to the components that are normally housed in the cavity. In this way, different components can be cleaned or replaced with those having different gear ratios, sizes, or orientations, in embodiments.

For example, the compact catheter manipulator can further include a plurality of planetary gears and a plurality of miter gears configured to mechanically couple the plurality of active rollers to the ring gear, wherein each of the plurality of planetary gears and the plurality of miter gears are arranged within the cavity. The active rollers can be configured to actuate at a speed proportional to the difference of rotation between the base gear and the ring gear. The base gear can be coupled to a first stationary motor and the ring gear can be coupled to a second stationary motor.

A plurality of corresponding miter gears can be coupled to associated ones of the plurality of miter gears, and each of the plurality of miter gears can extending through the housing. As such, when the housing is in place the miter gears are housed in the cavity whereas portions of the corresponding miter gears extend outside of the cavity, where they can be bound together to provide compressive force. The compressive force can then be transmitted back to the miter gears to which the corresponding miter gears share an axis of rotation. The plurality of corresponding miter gears can be coupled to one another via an elastomeric band to provide such compressive force.

Although the embodiments described with respect to the Figures are specific to routing of a catheter in an MRI setting, alternative embodiments could be used in various other contexts and settings. For example, in embodiments a catheter can be routed by a system similar to those described herein, without using MRI in conjunction. In still further embodiments, systems are configured to route a device other than a catheter such as a fiber optic cable, a fish tape, or a power line in areas with limited working space. For many such systems, the use of a remote robot system can be beneficial both because of its smaller space requirements compared to conventional systems, and because such settings can be hazardous to human operators when conventional non-remote systems are used.

Various embodiments of systems, devices, and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A tele-robotic system for remote manipulation of a catheter having a catheter handle and a catheter plunger, the system comprising:
   a plunger actuator comprising:
      a first motor mechanically coupled to a winch, wherein the winch is further mechanically coupled to the catheter plunger, and
      a second motor mechanically coupled to a rotatable gantry, wherein the rotatable gantry is further coupled to a catheter housing configured to hold the catheter handle; and
   a compact catheter manipulator comprising:
      a third motor mechanically coupled to a first geartrain, and a fourth motor mechanically coupled to a second geartrain, wherein the first geartrain and the second geartrain cooperate to manipulate radial and axial movement of the catheter.

2. The system of claim 1, wherein the first geartrain comprises:
   a first drive gear mechanically coupled to the third motor; and
   a base gear mechanically coupled to the first drive gear and configured to rotate the catheter.

3. The system of claim 2, wherein the second geartrain comprises:
   a second drive gear mechanically coupled to the fourth motor;
   a ring gear mechanically coupled to the second drive gear;
   a plurality of planetary gears mechanically coupled to the ring gear; and
   a plurality of miter gears mechanically coupled to the plurality of planetary gears to cause rotation of a plurality of active rollers.

4. The system of claim 2, wherein the base gear is further coupled to the miter gears such that a rotational speed of the miter gears is proportional to the difference of a rotational speed of the base gear and a rotational speed of the ring gear.

5. The system of claim 1, wherein the compact catheter manipulator further comprises a plurality of idle rollers, and wherein the idle rollers are mechanically coupled to one another via a binding device, wherein the binding device is selected from the group consisting of an elastomeric device, a spring device, or a clamping device.

6. The system of claim 5, wherein the idle rollers are adapted to receive any catheter having a size within a range.

7. The system of claim 1, wherein the plunger actuator is made of non-magnetic materials.

8. A method of manipulating a catheter having a catheter handle and a catheter plunger, the method comprising:
   providing a plunger actuator comprising:
      a first motor mechanically coupled to a winch, wherein the winch is further coupled to the catheter plunger, and
      a second motor mechanically coupled to a rotatable gantry, wherein the rotatable gantry is further coupled to a catheter housing configured to hold the catheter handle; and
   providing a compact catheter manipulator comprising:
      a third motor mechanically coupled to a first geartrain, and a fourth motor mechanically coupled to a second geartrain, wherein the first geartrain and the second geartrain cooperate to manipulate radial and axial movement of the catheter.

9. The method of claim 8, further comprising providing the catheter, wherein the catheter is configured to be manipulated by the compact catheter manipulator.

10. The method of claim 9, and further comprising providing an elastomeric band that can be coupled with the compact catheter manipulator to hold the catheter.

11. The method of claim 10, wherein the elastomeric band and the compact catheter manipulator are configured to hold any catheter having a diameter of between about 3 Fr and about 15 Fr.

* * * * *